United States Patent
Lin et al.

(10) Patent No.: US 7,186,799 B2
(45) Date of Patent: *Mar. 6, 2007

(54) PEPTIDE AND AMINE EXAMINATION METHOD USING THE SAME

(75) Inventors: Yuh-Jiuan Lin, Taipei (TW); Hong-Ru Guo, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 558 days.

This patent is subject to a terminal disclaimer.

(21) Appl. No.: 10/262,832

(22) Filed: Oct. 3, 2002

(65) Prior Publication Data

US 2003/0119065 A1    Jun. 26, 2003

(30) Foreign Application Priority Data

Dec. 21, 2001   (TW) ............................... 90131930 A

(51) Int. Cl.
*A61K 38/08*    (2006.01)
*G01N 33/00*    (2006.01)
*C12M 1/34*    (2006.01)

(52) U.S. Cl. .................. 530/329; 436/111; 436/112; 436/113; 435/287.1

(58) Field of Classification Search ................ 530/329; 436/111–113; 435/287.1
See application file for complete search history.

(56) References Cited

U.S. PATENT DOCUMENTS

2005/0074817 A1 *  4/2005  Lin et al. ..................... 435/7.1

FOREIGN PATENT DOCUMENTS

WO         01/27158 A2 *  4/2001

OTHER PUBLICATIONS

Lehninger et al. (1993) Principles of Biochemistry, Second Edition, Worth Publishers: New York, NY, p. 125.*
Wu, T-Z. (1999) "A piexoelectric biosensor as an olfactory receptor for odour detection: electronic nose" Biosensors & Bioelectronics 14:9-18.*
Wu, T-Z et al., "Synthetic peptide mimicking of binding sites on olfactory receptor protein for use in 'electronic nose'" (2000) J. Biotechnology 80:63-73.*
Wu, T-Z et al., "Exploring the recognized bio-mimicry materials for gas sensing" (2001) Biosensors & Bioelectronics 16:945-953.*
Merck Manual Home Edition, Merck, Inc., the sections "Symptoms and Diagnosis of Kidney and Urinary Tract Disorders" "Chronic Renal Failure", "Liver and Gallbladder Disorders", and "Peptic Ulcer". Downloaded from www.merck.com on Feb. 6, 2006.*

* cited by examiner

*Primary Examiner*—Long V. Le
*Assistant Examiner*—Christine Foster
(74) *Attorney, Agent, or Firm*—Sughrue Mion, PLLC

(57) ABSTRACT

A peptide for detecting amine, and a method and apparatus for detecting amines using the peptide. The method comprises the application of a sensor to examine a sample, wherein the sensor is coated with the peptide. The result collected from the sensor is compared with a database to determine the amount of amine presenting in the sample.

12 Claims, 4 Drawing Sheets

PEPTIDE AND AMINE EXAMINATION METHOD USING THE SAME

BACKGROUND OF THE INVENTION

SEQUENCE LISTING

| | |
|---|---|
| Asp-Pro-Asp-Gln-Arg-Asp; | SEQ ID NO:1 |
| Gly-Asp-Leu-Glu-Ser-Phe; | SEQ ID NO:2 |
| Glu-Tyr-Asp-Ser-Cys. | SEQ ID NO:3 |

1. Field of the Invention

The present invention relates to a peptide. In particular, the present invention relates to a peptide with high binding sensitivity and strong binding affinity that is suitable for amine examination. The present invention also relates to a method and apparatus for detecting amine using the peptide.

2. Description of the Related Art

Olfactory proteins are present on the nasal mucosa of mammal olfactory organs. When an olfactory protein reacts with an odorant molecule, a signal is generated, passed through a cascade of biochemical reactions, and delivered to the sensory area in the brain, where the smell is recognized. An olfactory protein has different binding sites for different odorant molecules. A binding site has a unique amino acid sequence that forms a unique three dimensional structure (tertiary structure) to bind the specific odorant molecule. Based on this theory, it is assumed that different amino acid sequences bind to different odorant molecules or odorant compounds with various affinity. The present invention uses various peptides as the receptor of a sensor to examine the amine content of a sample.

SUMMARY OF THE INVENTION

The object of the present invention is to provide a peptide with high binding sensitivity and strong binding affinity. The peptide of the present invention is useful in detecting amines.

The present invention also provides an amine examination method using the peptide. The method comprises the application of a sensor to examine a sample, wherein the sensor is coated with the peptide. The result collected from the sensor is compared with a database to determine the amount of amine presenting in the sample. The method is particularly useful in diagnosis of disorders accompanied with elevated amine levels.

The present invention also provides an apparatus for detecting amines using the peptide. The apparatus comprises a sensor coated with the peptide, and a signal processing device coupled with the sensor to generate a signal.

Amine compounds have low olfactory threshold, and are especially difficult to detect when present in trace amounts or low concentration. The peptide of the present invention features in high binding sensitivity and binding affinity to amine compounds. When the peptide is applied to a sensor for the examination of amine compounds, it provides a sensitive tool for detecting amine, even when the amine is present only in a very low concentration.

BRIEF DESCRIPTION OF THE DRAWINGS

The present invention can be more fully understood by reading the subsequent detailed description in conjunction with the examples and references made to the accompanying drawings, wherein.

Abbreviations:
Trimethylamine: TMA,
Dimethylamine: DMA,
Monomethylamine: MMA,
Ammonia: $NH_3$.

DETAILED DESCRIPTION OF THE PREFERRED EMBODIMENT

Many disorders are accompanied by elevated amine levels with detectable presence in the breath. Such disorders include kidney disease, uremia, liver disease, stomach ulcer and others. The disorder therefore can be diagnosed through determining the amine level in the breath. A way to apply the present invention in the diagnosis of such disorder is to build a database containing data of normal amine levels in breath and in the subject's breath using the peptide of the present invention. When the diagnosis is carried out, the amine content is measured using the peptide of the present invention. By comparing the measured amine level to the database, the subject's condition is determined.

Another application of the present invention is testing freshness of seafood. Spoiled seafood such as fish and shellfish releases amine compounds. Therefore, the freshness of seafood can be tested by determining the level of amine compounds released using the peptide of the present invention.

Similarly, another application of the present invention is testing air or water quality by determining amine levels in air or water, respectively.

The design of the peptide of the present invention was based on the analysis of secondary structure of the olfactory protein, and the simulation of the binding site between the tertiary structure of the olfactory protein and the target ordorant molecule. The physical and chemical properties of the substance to be examined were also considered. The peptide can be deduced from natural source or be synthetic. Together with a sensor such as a biochip, the peptide is used for detecting amine.

"Amine" or "amine compound" herein means a compound having a $NR_3$ group. R is an alkyl group or an aryl group. Examples of $NR_3$ group in the present invention are trimethylamine, dimethylamine, monomethylamine and ammonia groups.

The peptide of the present invention is one of the following:

```
Asp-Pro-Asp-Gln-Arg-Asp,        SEQ ID NO:1

Gly-Asp-Leu-Glu-Ser-Phe, or     SEQ ID NO:2

Glu-Tyr-Asp-Ser-Cys.            SEQ ID NO:3
```

One or more modifying groups can be added to the C- and/or N-terminals of the peptide if desired. The modifying group can be an amino acid or other functional group. Examples of amino acid include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Examples for functional group include —COOH, —NH2, —CHO, —OH, or —SH group, wherein —SH group is more preferred.

Figure 1:
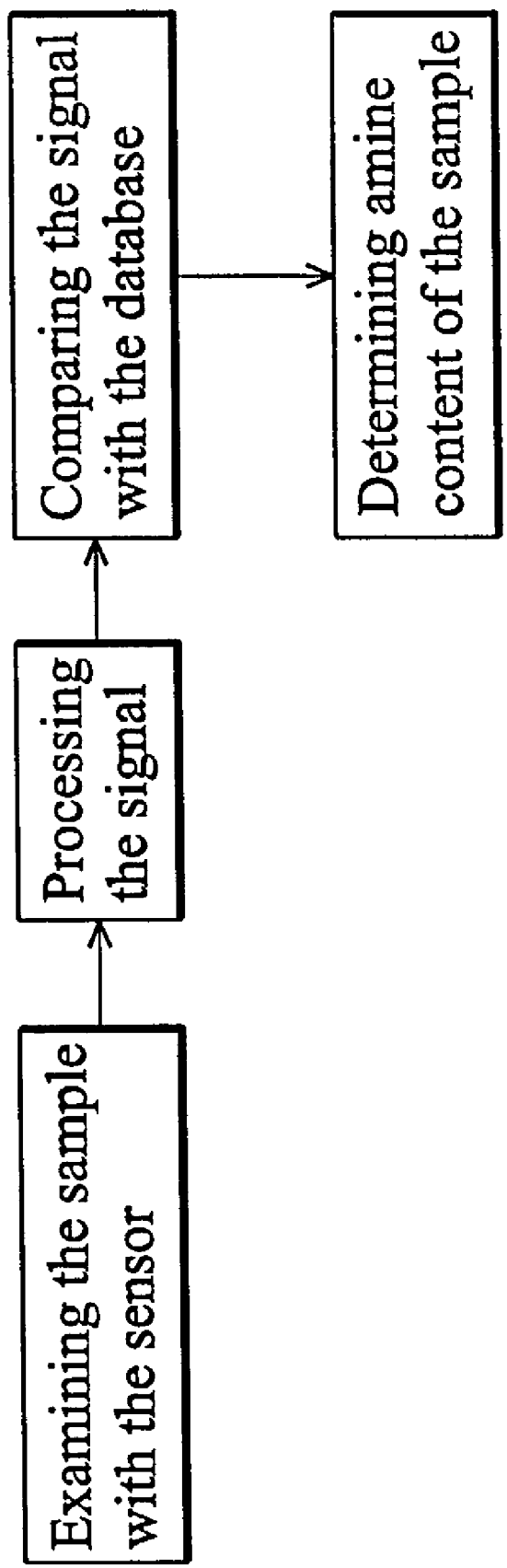
FIG. 1 is a flow chart of the an amine examination method using the peptide of the present invention.

The method of the present invention utilizes the previously described peptide to determine the level of amine present in a sample. FIG. 1 is a flow chart of the method for detecting amine using a peptide of the present invention. The method comprises the application of a sensor to examine a sample, wherein the sensor is coated with the peptide. The result collected from the sensor is then processed and compared with a database to determine the quantity of amine presenting in the sample. "Amine" herein means a compound having a $NR_3$ group, wherein R is an alkyl group or an aryl group. For the present invention preferred $NR_3$ group includes trimethylamine, dimethylamine, monomethylamine and ammonia groups.

When the examination is carried out, the sensor is presented with a sample. The amine content of the sample is determined based on the binding of the peptide and the amine. The sensory device can be a transducer such as a biochip, piezoelectric quartz crystal, surface acoustic wave, electrochemical, fiber optic, surface plasmon resonance, or metal oxide semiconductor.

Piezoelectric quartz crystal biological sensor is one of the most promising sensors currently in use. A preferred embodiment of the present invention uses a piezoelectric quartz crystal biological sensor. The sensor comprises a piezoelectric quartz crystal and the previously described peptide, wherein the peptide is coated on the piezoelectric quartz crystal to form a sensor. When the peptide reacts and binds to an amine molecule, the frequency of the piezoelectric quartz crystal changes due to the changed mass. The resulting piezoelectric quartz crystal biological sensor of the present invention detects amine with high sensitivity and specificity.

According to the method of the present invention, the sample can be gas, liquid, or solid. For example, the sample can be air, breath, water, seafood, body fluid such as blood or urea of a live subject, or volatile vapor of body fluid of such a subject.

The amine examination method of the present invention has a wide variety of applications. For example, the present invention can be used to diagnose disorders accompanied by elevated amine levels detectable in the breath. Such disorders include kidney disease, uremia, liver disease, stomach ulcers and others. Other applications include freshness testing of seafood, air quality testing, and water quality testing.

The apparatus for detecting amine according to the present invention comprises a sensory device, a peptide as previously described, and a signal process device coupled to the sensory device, wherein the peptide is coated on the sensory device. The sensory device can be chemical or physical sensor with a transducer, or a biological sensor such as a biochip. Transducer of the sensory device can be, for example, piezoelectric quartz crystal, surface acoustic wave, electrochemical sensor, fiber optic, surface plasmon resonance, or metal oxide semiconductor.

Without intending to limit it in any manner, the present invention will be further illustrated by the following examples using a piezoelectric quartz crystal as the sensor.

Design of the Peptide

Tertiary structure of olfactory protein was used as a template in the computer program "Insight II" to simulate possible binding sites for amine compounds. The selected peptide sequence is then modified according to properties of different amino acids to obtain a peptide sequence that is both specific and sensitive in binding amine. The modified peptide is immobilized on the transducer as a receptor film. The transducer used in the embodiments is a 12 MHz piezoelectric quartz crystal, on which the peptide is coated. The amine examining apparatus is used in determining types and quantity of compounds containing amine groups in a sample.

PREPARATION EXAMPLE 1

Synthesis of the Peptide

The peptide of the present invention can be synthesized by conventional peptide synthesis techniques such as solid phase synthesis, liquid peptide synthesis, enzymatic synthesis, or recombinant DNA technology. The peptide used in this example is synthesized by solid phase synthesis using Wang resin as the resin and F-moc as the protecting group in a Peptide Synthesizer (Apply Biosystems, 432A Peptide Synthesizer, USA).

PREPARATION EXAMPLE 2

Modification of the Peptide and Coating the Peptide on the Piezoelectric Quartz Crystal A cysteine is attached to the C- or N-terminal of the peptide of the present invention. The peptide is then dissolved and diluted in a suitable organic solvent. A 12 MHz piezoelectric quartz crystal with a gold electrode is used in this example. 2–4 μl of the peptide solution was applied to the gold electrode for 4 hours for the peptide to be immobilized on the gold electrode. The cysteine at the terminal of the peptide has a —SH group, wherein the sulfur atom forms a very steady covalent bond with the gold molecules of the electrode. The apparatus is ready for use when the detected frequency decrement is between 15000 and 20000 Hz. The procedure of coating the peptide to the sensory device is adjusted according to different properties of the peptide.

PREPARATION EXAMPLE 3

Preparation of Volatile Vapor

Reagent grade trimethylamine, dimethylamine, monomethylamine, ammonia, acetone, formic acid, butyric acid, ethyl acetate, ethanol and formaldehyde were separately dissolved in 5 ml of volatile organic solvent. The solution was sealed in separate 120 ml containers for 5 days allowing the space above the solution to reach the saturate vapor pressure. The concentration of the saturate vapor was calculated from the concentration of the solution and the saturate vapor pressure. The saturate vapor was used for the analysis with or without dilution.

EXAMPLE 1

An amine examining apparatus according to the present invention is formed by coating the peptide of SEQ ID NO:1 to a piezoelectric quartz crystal according to the procedure described in Preparation Example 2. The amine examining apparatus was tested with volatile vapor of trimethylamine, dimethylamine, monomethylamine, ammonia, acetone, formic acid, butyric acid, ethyl acetate, ethanol and formaldehyde prepared according to Preparation Example 3 and the results were analyzed by an analysis system (Smart Biotechnology Co., Ltd., Taipei, Taiwan). The volatile vapor used in the test is about 5 mg/l per test. The specificity and sensitivity of the amine examining apparatus towards each of the previously mentioned volatile vapor were tested.

Figure 2:
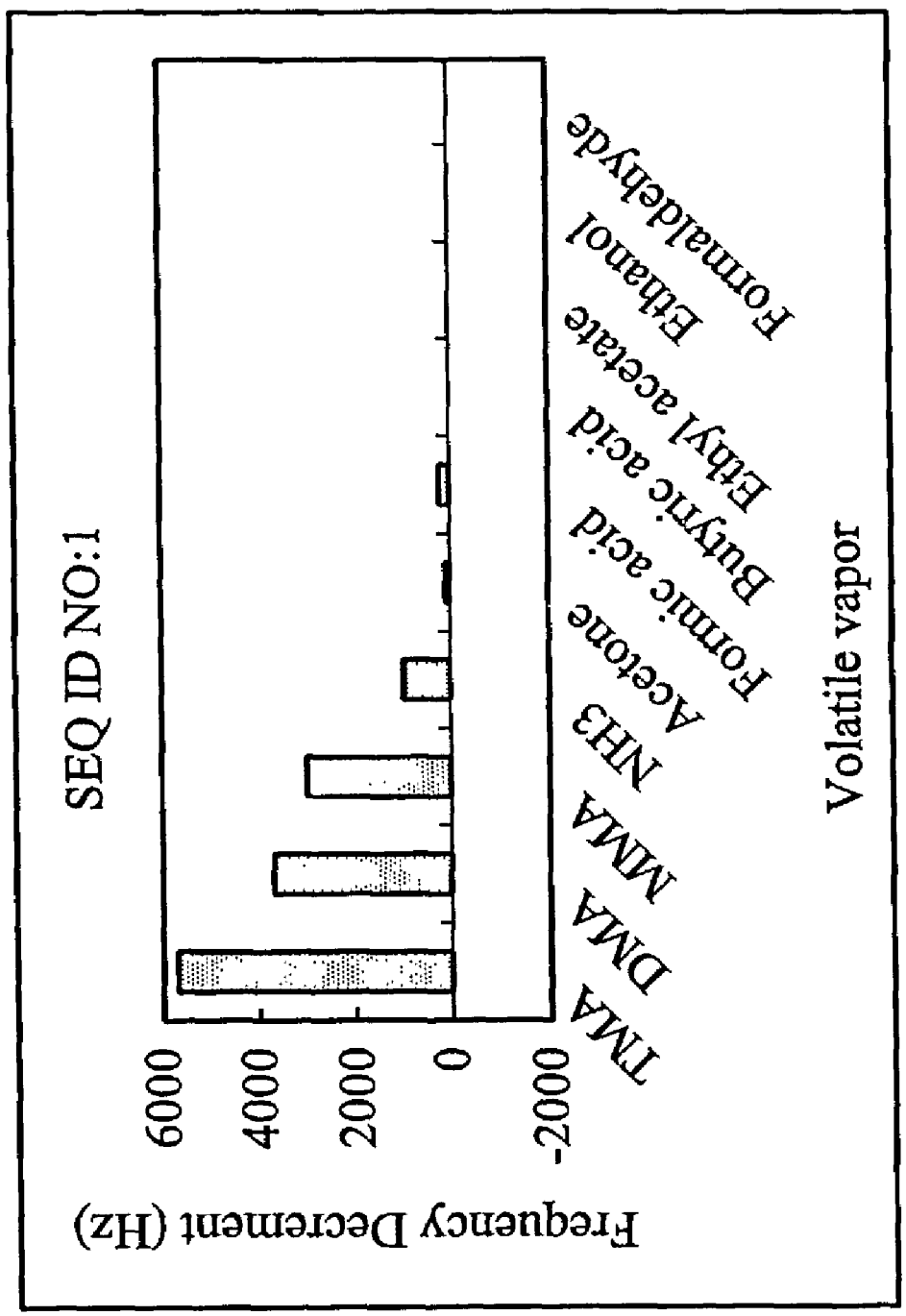
FIG. 2 is a comparative diagram showing frequency decrement when peptide with SEQ ID NO:1 reacts with different compounds.

According to Sauerbrey equation (Sauerbrey, 1959), frequency decrement of a piezoelectric quartz crystal is proportional to the mass applied to the piezoelectric quartz crystal. Therefore the coating quantity of peptide is indicated by the frequency decrement (Hz) after the peptide is coated on the piezoelectric quartz crystal. For this example, coating quantity of SEQ ID NO:1 peptide was 2194 Hz. The frequency decrement when SEQ ID NO:1 peptide reacted with volatile vapor of trimethylamine, dimethylamine, monomethylamine, ammonia, acetone, formic acid, butyric acid, ethyl acetate, ethanol and formaldehyde was shown in FIG. 2. FIG. 2 depicts that SEQ ID NO:1 peptide bound to trimethylamine, dimethylamine, monomethylamine, and ammonia particularly well, while it bound to other chemicals at very low rates. The results indicate that SEQ ID NO:1 peptide has high specificity and sensitivity in binding with trimethylamine, dimethylamine, monomethylamine, and ammonia. Therefore SEQ ID NO:1 peptide is a very suitable tool in detecting compounds containing amine groups.

EXAMPLE 2

An amine examining apparatus according to the present invention is formed by coating the peptide of SEQ ID NO:2 to a piezoelectric quartz crystal according to the procedure described in Preparation Example 1. The amine examining apparatus was tested with volatile vapor of trimethylamine, dimethylamine, monomethylamine, ammonia, acetone, formic acid, butyric acid, ethyl acetate, ethanol and formaldehyde prepared according to Preparation Example 3 and the results were analyzed by an analysis system (Smart Biotechnology Co., Ltd., Taipei, Taiwan). The volatile vapor used in the test is about 5 mg/l per test. The specificity and sensitivity of the amine examining apparatus towards each of the previously mentioned volatile vapor were tested.

Figure 3:
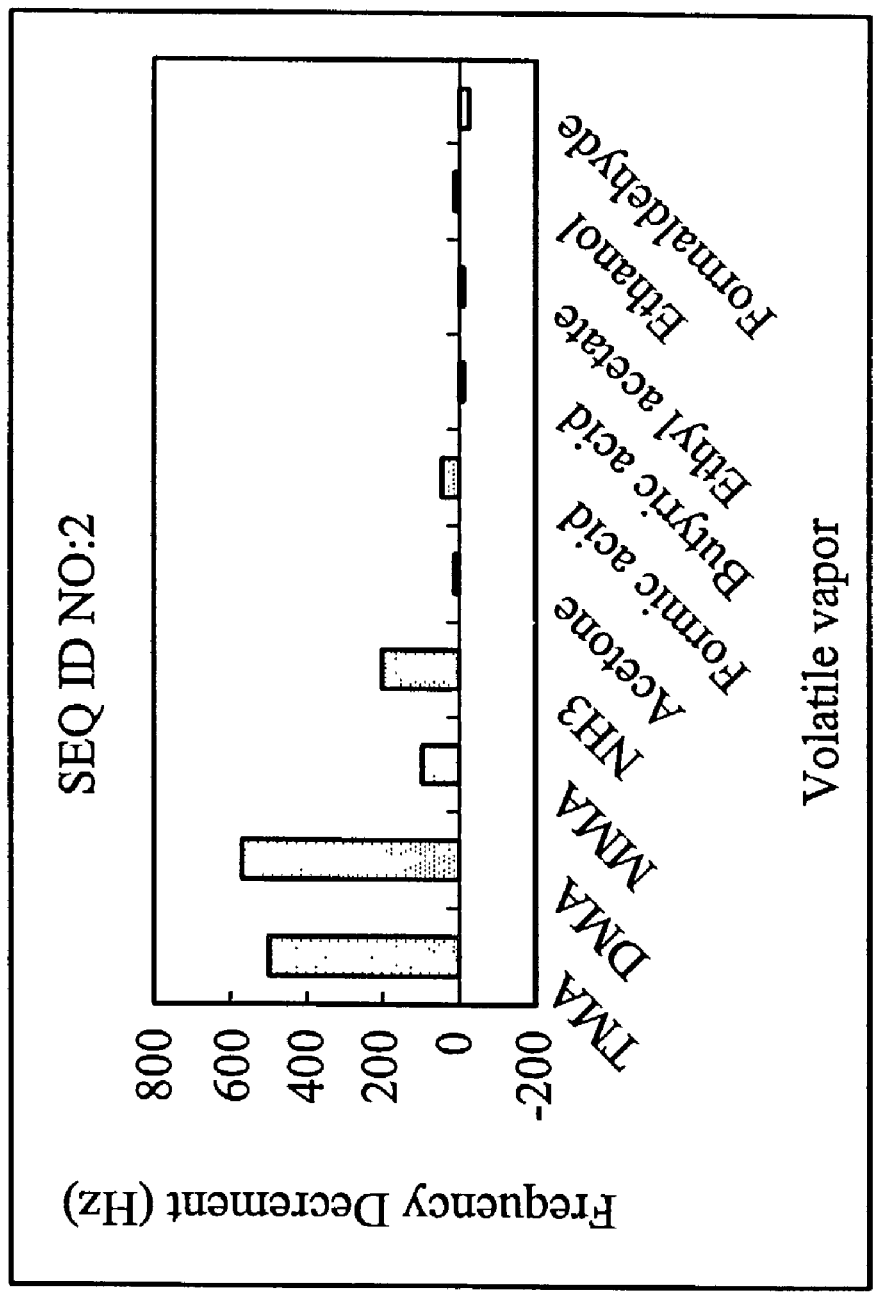
FIG. 3 is a comparative diagram showing frequency decrement when peptide with SEQ ID NO:2 reacts with different compounds.

For this example, coating quantity of SEQ ID NO:2 peptide was 283 Hz. The frequency decrement when SEQ ID NO:2 peptide reacted with volatile vapor of trimethylamine, dimethylamine, monomethylamine, ammonia, acetone, formic acid, butyric acid, ethyl acetate, ethanol and formaldehyde was shown in FIG. 3. FIG. 3 depicts that SEQ ID NO:2 peptide bound to trimethylamine, dimethylamine, monomethylamine, and ammonia particularly well, while it bound to other chemicals at very low rates. The results indicate that SEQ ID NO:2 peptide has high specificity and sensitivity in binding with trimethylamine, dimethylamine, monomethylamine, and ammonia. Therefore SEQ ID NO:2 peptide is a very suitable tool in detecting compounds containing amine groups.

EXAMPLE 3

An amine examining apparatus according to the present invention is formed by coating the peptide of SEQ ID NO:3 to a piezoelectric quartz crystal according to the procedure described in Preparation Example 1. The amine examining apparatus was tested with volatile vapor of trimethylamine, dimethylamine, monomethylamine, ammonia, acetone, formic acid, butyric acid, ethyl acetate, ethanol and formaldehyde prepared according to Preparation Example 3 and the results were analyzed by an analysis system (Smart Biotechnology Co., Ltd., Taipei, Taiwan). The volatile vapor used in the test is about 5 mg/l per test. The specificity and sensitivity of the amine examining apparatus towards each of the previously mentioned volatile vapor were tested.

Figure 4:
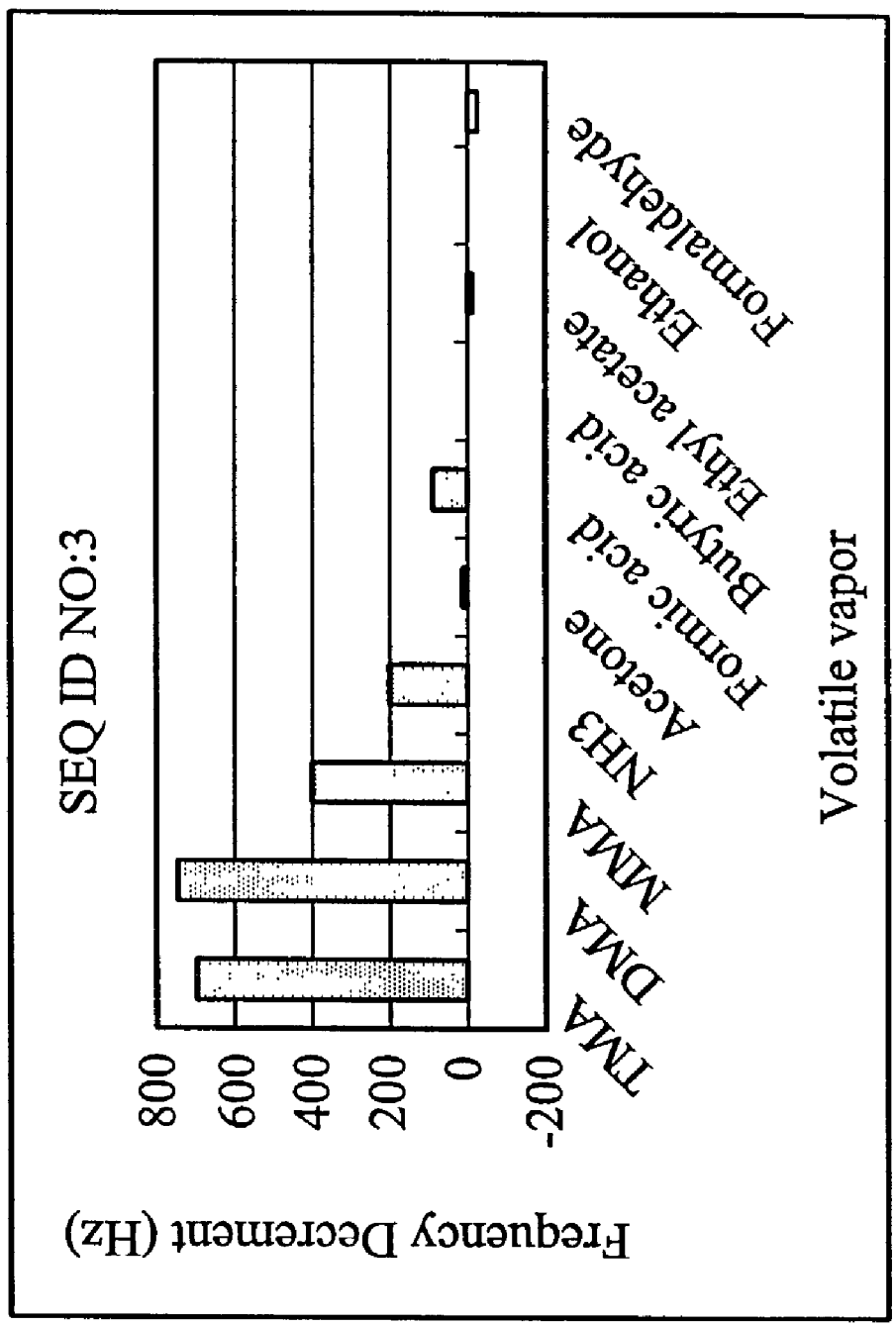
FIG. 4 is a comparative diagram showing frequency decrement when peptide with SEQ ID NO:3 reacts with different compounds.

For this example, coating quantity of SEQ ID NO:3 peptide was 620 Hz. The frequency decrement when SEQ ID NO:3 peptide reacted with volatile vapor of trimethylamine, dimethylamine, monomethylamine, ammonia, acetone, formic acid, butyric acid, ethyl acetate, ethanol and formaldehyde was shown in FIG. 4. FIG. 4 depicts that SEQ ID NO:3 peptide bound to trimethylamine, dimethylamine, monomethylamine, and ammonia particularly well, while it bound to other chemicals at very low rates. The results indicate that SEQ ID NO:3 peptide has high specificity and sensitivity in binding with trimethylamine, dimethylamine, monomethylamine, and ammonia. Therefore SEQ ID NO:3 peptide is a very suitable tool in detecting compounds containing amine groups.

Finally, while the invention has been described by way of example and in terms of the preferred embodiment, it is to be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. An isolated peptide, consisting of SEQ ID NO:1.

2. An amine detecting apparatus comprising a sensory device coated with the isolated peptide as set forth in claim 1, and a signal process device coupled to the sensory device.

3. The amine detecting apparatus as set forth in claim 2, wherein the sensory device is a piezoelectric quartz crystal, surface acoustic wave, electrochemical sensor, fiber optic, surface plasmon resonance, or metal oxide semiconductor.

4. The amine detecting apparatus as set forth in claim 2, wherein the sensory device is a biochip.

5. An amine detecting method, comprising:
   providing a sensory device coated with the isolated peptide as set forth in claim 1;
   contacting the sensory device with a sample; and
   detecting the level of amine present in the sample.

6. The amine detecting method as set forth in claim 5, wherein the sensory device is a piezoelectric quartz crystal, surface acoustic wave, electrochemical sensor, fiber optic, surface plasmon resonance, or metal oxide semiconductor.

7. The amine detecting method as set forth in claim 5, wherein the sensory device is a biochip.

8. The amine detecting method as set forth in claim 5, wherein the amine is trimethylamine, dimethylamine, monomethylamine, or ammonia.

9. The amine detecting method as set forth in claim 5, wherein the sample is water, air, animal breath, body fluid of an animal, blood of an animal, urine of an animal, fish or seafood.

10. The amine detecting method as set forth in claim 5, wherein the sample is human breath.

11. The amine detecting apparatus as set forth in claim 2, wherein the isolated peptide is attached at the C- or N-terminus to the sensory device through a cysteine group.

12. The amine detecting method as set forth in claim 5, wherein the isolated peptide is attached at the C- or N-terminus to the sensory device through a cysteine group.

* * * * *

SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Peptide for amine detection

```
<400> SEQUENCE: 1

Asp Pro Asp Gln Arg Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Peptide for amine detection

<400> SEQUENCE: 2

Gly Asp Leu Glu Ser Phe
1               5

<210> SEQ ID NO 3
<211> LENGTH: 5
<212> TYPE: PRT
<213> ORGANISM: Artificial Sequence
<220> FEATURE:
<223> OTHER INFORMATION: Peptide for amine detection

<400> SEQUENCE: 3

Glu Tyr Asp Ser Cys
1               5
```